United States Patent [19]

Pagan

[11] Patent Number: 5,983,897
[45] Date of Patent: Nov. 16, 1999

[54] LARYNGEAL MASK ASSEMBLIES

[75] Inventor: Eric Pagan, Hythe, United Kingdom

[73] Assignee: Smiths Industries Public Limited Company, London, United Kingdom

[21] Appl. No.: 09/037,992

[22] Filed: Mar. 11, 1998

[30] Foreign Application Priority Data

Mar. 18, 1997 [GB] United Kingdom .................... 9705586

[51] Int. Cl.$^6$ .................................................. A61M 16/00
[52] U.S. Cl. ................................ 128/207.15; 128/200.26; 128/207.14; 604/96
[58] Field of Search .......................... 128/206.26, 207.14, 128/207.15, 200.26; 604/96–103

[56] References Cited

U.S. PATENT DOCUMENTS

| | | | |
|---|---|---|---|
| 4,509,514 | 4/1985 | Brain | 128/207.15 |
| 4,995,388 | 2/1991 | Brain . | |
| 5,241,956 | 9/1993 | Brain . | |
| 5,249,571 | 10/1993 | Brain . | |
| 5,282,464 | 2/1994 | Brain . | |
| 5,297,547 | 3/1994 | Brain . | |
| 5,303,697 | 4/1994 | Brain . | |
| 5,305,743 | 4/1994 | Brain . | |
| 5,584,290 | 12/1996 | Brain | 128/207.15 |
| 5,771,889 | 6/1998 | Pagan . | |
| 5,878,745 | 3/1999 | Brain | 128/207.15 |
| 5,881,726 | 3/1999 | Neame | 128/207.15 |
| 5,896,858 | 4/1999 | Brain | 128/207.15 |
| 5,937,859 | 8/1999 | Augustine et al. | 128/207.15 |
| 5,937,860 | 8/1999 | Cook | 128/207.15 |

FOREIGN PATENT DOCUMENTS

| | | |
|---|---|---|
| 0 448 878 | 10/1991 | European Pat. Off. . |
| 2111394 | 7/1983 | United Kingdom . |
| 2128561 | 5/1984 | United Kingdom . |
| 2205499 | 12/1988 | United Kingdom . |
| 2249959 | 5/1992 | United Kingdom . |
| 2267034 | 11/1993 | United Kingdom . |

*Primary Examiner*—John G. Weiss
*Assistant Examiner*—Joseph F. Weiss, Jr.
*Attorney, Agent, or Firm*—Pollock, Vande Sande & Amernick

[57] ABSTRACT

A laryngeal mask assembly has a mask portion formed by a mount with a plate to which inflatable cuffs are attached on both sides. The plate projects beyond the cuffs to form a non-inflatable leading tip to aid insertion of the assembly into the patient.

5 Claims, 1 Drawing Sheet

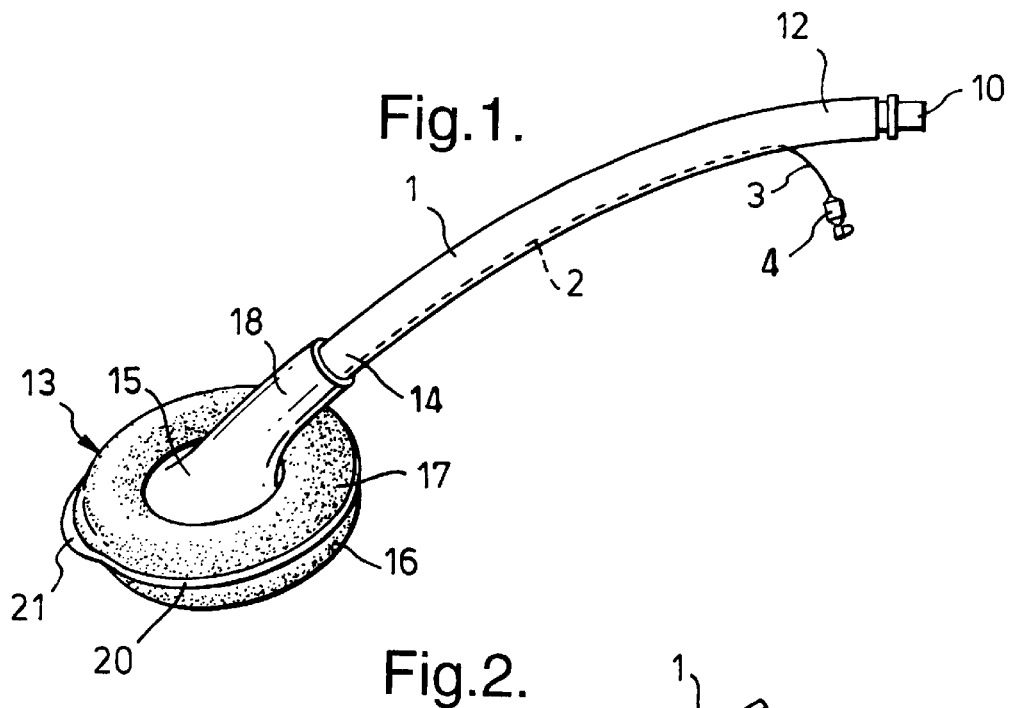
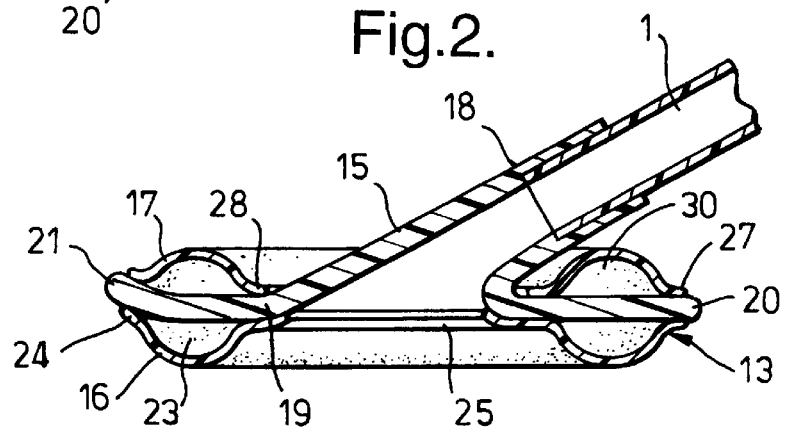
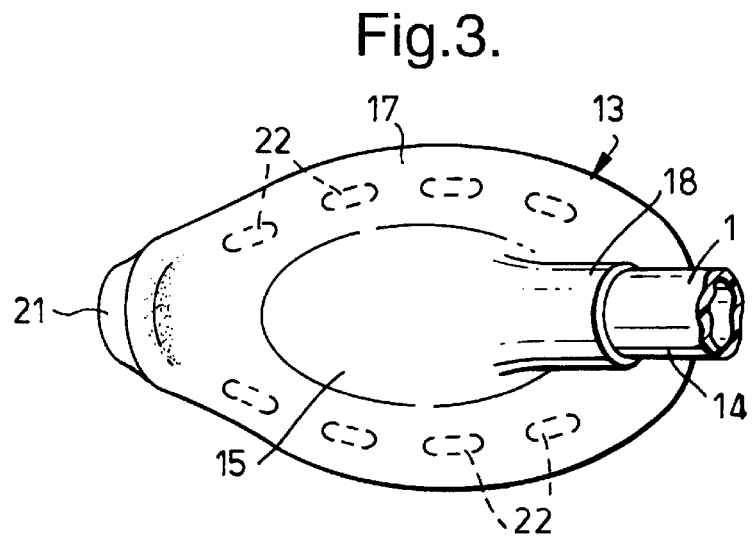

LARYNGEAL MASK ASSEMBLIES

BACKGROUND OF THE INVENTION

This invention relates to laryngeal mask assemblies

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. Nos. 5,355,879, 5,305, 743, 5,297,547, 5,282,464, GB 2267034, U.S. Pat. Nos. 5,249,571, 5,241,956, 5,303,697, GB 2249959, GB 2111394, EP 448878, U.S. Pat. No. 4,995,388, GB 2205499, GB 2128561 and U.S. Pat. No. 5,771,889.

Laryngeal masks have several advantages over endotracheal tubes, which are longer and seal with the trachea below the vocal folds. One problem with laryngeal mask airways, however, is that they can be difficult to introduce correctly into a patient, especially by an inexperienced user.

BRIEF SUMMARY OF THE INVENTION

It is an object of the present invention to provide an improved laryngeal mask assembly.

According to the present invention there is provided a laryngeal mask assembly comprising a tube with a mask portion at its patient end, the tube opening into the center of the mask portion and the mask portion having an inflatable cuff member of generally oval shape for providing a seal with patient tissue in the region of the hypopharynx, the mask portion including a tip member projecting beyond the cuff member to aid insertion of the assembly into a patient.

The mask portion preferably comprises a mount member attached with the patient end of the tube, the cuff member being attached with the mount member and the tip member being provided by a part of the mount member. The mount member preferably comprises a sleeve attached with the tube and a plate member projecting at an angle to the sleeve, the tip member being provided by a part of the plate member. The tip member may be provided by a curved up leading edge of the plate member. The assembly preferably includes two cuff members attached to opposite sides of the mount member.

A laryngeal mask airway assembly according to the present invention, will now be described, by way of example, with reference to the accompanying drawing.

BRIEF DESCRIPTION OF THE DRAWING

FIG. 1 is a side elevation view of the assembly;

FIG. 2 is a sectional side elevation view of the patient end of the assembly to an enlarged scale; and FIG. 3 is a view from above of the patient end of the assembly.

DETAILED DESCRIPTION OF THE PREFERRED EMBODIMENT

The assembly comprises a bendable tube 1 of a plastics material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 opens into the mask portion 13.

The mask portion 13 comprises a mount member 15 and two cuff members 16 and 17. The mount member 15 is moulded from a bendable plastics material, such as PVC. The mount member 15 has a hollow cylindrical sleeve 18 at its rear end, in which the forward, patient end 14 of the tube 1 is inserted and joined. The forward, patient end 19 of the mount member 15 has a substantially flat plate 20 with a generally elliptical or egg-shape outline, which projects outwardly of the sleeve 18 at an angle of about 30°. The forward edge of the plate 20 is curved upwardly to form a leading tip 21. Several air vent holes 22 are spaced around the plate 20 and allow air to flow through the thickness of the plate.

The cuff members 16 and 17 are both blow moulded from a flexible, resilient plastics material, such as PVC, polyurethane, silicone, EVA, TPE, polyether block amide or the like. The cuff members could be formed in other ways, such as by vacuum forming, pressure vacuum forming or injection moulding. Alternatively, the cuff members could be flat sheets, which might have elastomeric properties or be laminates with reinforcing. The lower, patient-end cuff member 16 has a semi-annular shape with a periphery conforming to the outline of the plate 20. An annular recess or channel 23 extends around the upper surface of the cuff member 16, within a peripheral rim 24. In the center of the cuff member 16 there is an aperture 25 of oval shape, which conforms to the shape of the opening of the patient end of sleeve 18. The cuff member 16 is bonded to the lower, patient side of the plate 20 both around the rim 24 and around the edge of the aperture 25 to enclose an annular space between the lower surface of the plate and the channel 23. The upper cuff member 17 is similar in shape to the lower cuff member 16 but is arranged upside down. The upper cuff member 17 has a peripheral rim 27 and an inner rim 28 bonded to the upper surface of the plate 20, on either side of an annular channel 30. The upper channel 30 communicates with the inflation lumen 2 by means of a channel in the mount member 15, or an interconnecting tube, so that gas supplied to the inflation lumen inflates the upper cuff member 17 and, because the gas flows through the air vents 22, it also inflates the lower cuff member 16.

The leading tip 21 projects forwardly slightly beyond the upper and lower cuff members 16 and 17 so as to provide a stiffer leading edge to help guide the mask portion 13 into the correct location in a patient.

What I claim is:

1. A laryngeal mask assembly comprising: a tube having a patient end and a machine end, a mask portion at the said patient end of said tube, said tube opening into a center of said mask portion, said mask portion having a non-inflatable mount member and an inflatable cuff member mounted on said mount member, said cuff member being of generally oval shape for providing a seal with patient tissue in the region of the hypopharynx, and said mount member including a tip portion projecting beyond said cuff member to provide a non-inflatable extension beyond said cuff member to aid insertion of said assembly into a patient.

2. A laryngeal mask assembly according to claim 1, wherein said mount member comprises a sleeve attached with said tube and a plate member projecting at an angle to said sleeve, and wherein said tip portion is provided by a part of said plate member.

3. A laryngeal mask assembly according to claim 2, wherein said tip portion is provided by a curved up leading edge of said plate member.

4. A laryngeal mask assembly according to claim 1, wherein said assembly includes two cuff members attached to opposite sides of said mount member.

5. A laryngeal mask assembly comprising: a tube having a patient end and a machine end; and a mask portion at said patient end of said tube, said mask portion comprising a mount member and an inflatable cuff member of generally oval shape for providing a seal with patient tissue in the region of the hypopharynx, said mount member comprising a sleeve attached with said patient end of said tube and a plate member extending outwardly of said sleeve at an angle, said tube opening centrally of said plate member, said inflatable cuff member being attached around an edge with said mount member and a forward edge of said plate member extending to form a non-inflatable leading tip member that projects beyond said inflatable cuff member to aid insertion of said assembly into a patient.

* * * * *